United States Patent
Levy

Patent Number: 5,599,610
Date of Patent: Feb. 4, 1997

[54] TRILAMINATE FABRIC FOR SURGICAL GOWNS AND DRAPES

[75] Inventor: Harry Levy, Hollis Hills, N.Y.

[73] Assignee: Fabrite Laminating Corp., Wood-Ridge, N.J.

[21] Appl. No.: 192,040

[22] Filed: Feb. 4, 1994

[51] Int. Cl.⁶ .................................................. B32B 7/00
[52] U.S. Cl. ................. 442/261; 428/315.7; 428/315.9; 428/317.7; 428/91; 428/96; 428/97; 442/281; 442/318
[58] Field of Search .................................. 428/246, 252, 428/253, 315.7, 315.9, 317.7, 91, 96, 97

[56] References Cited

U.S. PATENT DOCUMENTS 5,109,548 5/1992 Balaban et al. ........................... 2/175
5,204,156 4/1993 Lumb et al. .............................. 428/96

Primary Examiner—Christopher Raimund
Attorney, Agent, or Firm—Charles I. Brodsky

[57] ABSTRACT

A washable, sterilizable article for hospital and medical garments is disclosed. The article exhibits high resistance to the penetration of fluids, blood and viruses while exhibiting a high rate of moisture vapor transmission. The article comprises: a first layer of woven or knit fabric; a second layer of a microporous polyurethane membrane; a third layer of a woven or knit fabric; a first polyether-polyurethane adhesive joining the first and second layers together; and a second polyether-polyurethane adhesive joining the second and third layers together. The second layer has a porosity of approximately 6 billion individual pores per square inch.

8 Claims, 1 Drawing Sheet

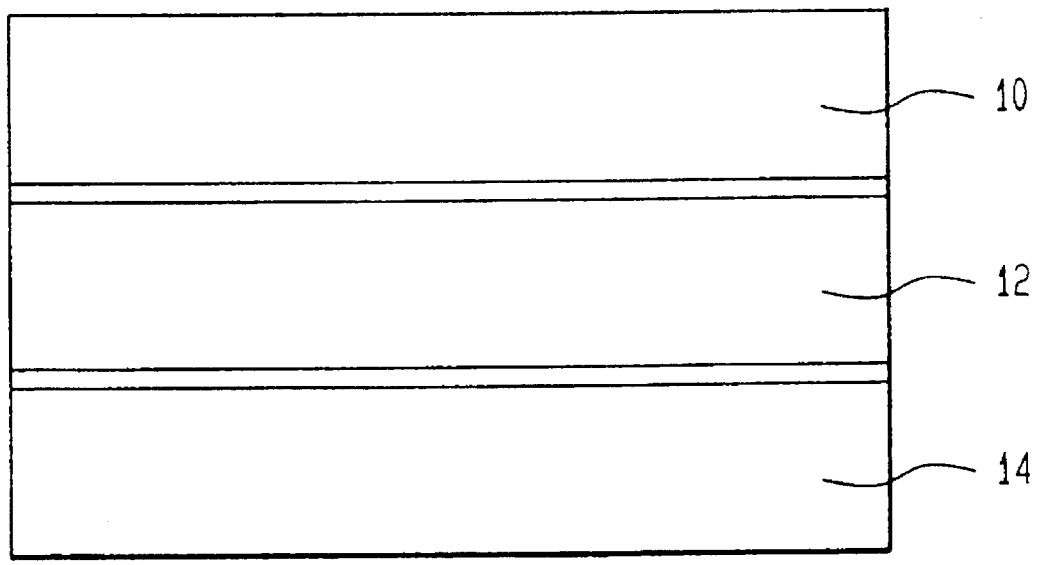

TRILAMINATE FABRIC FOR SURGICAL GOWNS AND DRAPES

FIELD OF THE INVENTION

This invention relates to surgical gowns, drapes and garments which are both washable and sterilizable after upwards of fifty and more commercial washings and dryings, and recommended autoclaving procedures.

BACKGROUND OF THE INVENTION

As is well known and understood, there is an extremely high risk to healthcare workers of viral disease transmission from infected patients. One of the more recent studies, for example, reported that almost 50 percent of operations resulted in at least one of the surgical room personnel becoming contaminated through cuts, pricks and splashes.

In view of studies such as this, regulations regarding occupational exposure to blood-borne pathogens have been developed under the Federal Occupational Safety and Health Administration ("OSHA") aegis. One such approach particularly concerned addressing a manner for minimizing the risk to both Human Immunodeficiency Virus (HIV) and Hepatitis B Virus (HBV); such regulation set forth that surgical gowns, drapes and other garment fabrics, to satisfy the federal guidelines, must exhibit specified resistance to fluid penetration and virus penetration, and must be washable and sterilizable. To keep the costs of healthcare as low as possible, these items must be capable of withstanding adverse washing and sterilization—either through commercial washings and dryers, or autoclavings, a minimum of 50 times at 275 degrees Fahrenheit, and for at least 5 minutes, according to OSHA.

As is also well known and understood, surgical gowns, drapes and other surgical garments must not only be "virus proof", but must also exhibit a high resistance to the penetration of water, blood and other fluids. To be completely usable, and as is known, they should also exhibit a high rate of moisture vapor transmission. Analysis has revealed that an estimated 5.6 million workers or more are estimated to be covered by this final OSHA regulation, inclusive of the entire healthcare sector of hospitals, nursing homes, out-patient facilities, medical and dental laboratories, linen services, handlers of regulated waste, etc. Thus, although there exists a great need for a surgical gown, drape and other surgical garment which is readily accepted as being needed to be impervious to blood and virus—besides being waterproof—, the need for such waterproof, breathable fabrics goes beyond just the operating room environment.

OBJECTS OF THE INVENTION

It is an object of the present invention, therefore, to provide a washable, sterilizable article for hospital and/or medical garment use which exhibits this very high resistance to the penetration of fluid, blood and virus, while exhibiting a high rate of moisture vapor transmission.

It is another object of the invention to provide such an article which can be washable and sterilizable to satisfy the OSHA regulations.

It is a further object of the invention to provide such an article in the nature of a fabric that will satisfy accepted Moisture Vapor Transmission Rate, Hydrostatic Resistance, Blood Resistance and Virus Resistance Tests set forth as industry standards to meet these OSHA regulations—as well as satisfying recommended standards of durability and reusability of these fabrics as employed in surgeons' gowns, surgical drapes, and other surgical garments worn in an operating room environment.

SUMMARY OF THE INVENTION

As will become clear hereinafter, the washable, sterilizable article of the invention comprises a trilaminate fabric consisting of a woven or knit fabric, a microporous polyurethane membrane, and another woven or knit fabric. As will also become clear, the microporous polyurethane membrane is laminated between the two fabrics with a polyetherpolyurethane adhesive. In accordance with the invention, furthermore, such microporous polyurethane membrane is composed of individual pores smaller than the smallest droplet of water, yet many times larger than a molecule of water vapor. With the preferred microporous polyurethane membrane composition to be described hereinafter, such microporous polyurethane membrane is composed of substantially 6 Billion individual pores per square inch, in a membrane substantially 0.012–0.055 mm in thickness.

With such construction embodying the invention as outlined above, the trilaminate has been tested to significantly prevent viruses, blood, water and other fluids from penetrating the fabric to reach the skin, while allowing a high moisture vapor transmission outwardly from the skin surface, as comforting for the wearer. Testing has also shown that the trilaminate essentially comprises a reusable fabric material that is able to withstand upwards of 50 commercial washings and autoclavings, and more, at 275 degrees Fahrenheit for periods at least as long as 5 minutes.

BRIEF DESCRIPTION OF THE DRAWING

These and other features of the invention will be more clearly understood from a consideration of the single FIGURE of the drawing showing the 3-layer trilaminate fabric construction of the washable, sterilizable article and their manners of securement.

DETAILED DESCRIPTION OF THE DRAWING

In accordance with the invention, a 3-layer trilaminate fabric is described which offers the features of laminating the face and back layers employed to the microporous polyurethane barrier membrane to provide a fluid impervious barrier which prevents passage of bacteria, virus, body fluids and other liquids, yet being breathable enough to be comfortable. In this regard, it will be understood that the face and back (i.e. top and bottom) layers of the surgical gown, surgical drape, and other surgical garment will thus take on the characteristics of being virusproof, waterproof, body fluid proof, and yet be a breathable laminate incorporating a woven or knitted fabric which is strong enough to withstand the high number of industrial washings and autoclavings required by the OSHA regulations.

Thus, referring to the drawing, the top, or face, layer fabric 10 incorporates, as was previously mentioned, a woven, or knit, fabric which may be a polyester, nylon, cotton, terrycloth, polypropylene, brushed polyester, brushed nylon, brushed cotton, or any suitable blend of these materials in woven or knit form. Such layer 10 serves as the top layer, or outward face, of the surgical material—and can be treated with different finishes to achieve such other desirable properties as low lint gathering, high abrasion resistance, high absorbancy and antistatic characteristics, a water and/or other fluid repellency, etc. In carrying out the teachings of the invention, a plain weave polyester of weight substantially 3.0±0.02 oz/yd$^2$ was found to be particularly useful.

The second layer 12 of the trilaminate incorporates, as also previously mentioned, a microporous polyurethane membrane to serve as a barrier to any fluids, including blood. In particular, the microporous polyurethane membrane 12 is selected, composed of individual pores smaller than the smallest droplet of water, yet many times larger than a molecule of water vapor—such as one composed of the order substantially of 6 Billion individual pores per square inch, to yield a pore size some 2,500 times larger than a molecule of water vapor. Typical of such microporous polyurethane barrier membranes is one available from Porvair plc. of King's Lynn, Norfolk, England, being sold under the tradename "Porelle". When having a preferred thickness of 0.012–0.055 mm, such microporous polyurethane membranes typically exhibit a water vapor permeability of 1,100 gm/m$^2$/24 hrs and 5,500 gm/m$^2$/24 hrs upright and inverted moisture vapor transmission rates respectively, with a hydrostatic resistance of 80 psi. As regards such membrane available from Porvair plc., microporous polyurethane membranes of this type have been noted to exhibit a very high resistance to abrasion, tearing and elongation of over 200% without deterioration of their integral properties. Such membranes have also been noted to exhibit high chemical resistance to alkali and detergent solutions.

The third layer of the trilaminate, according to the invention, is again of woven or knit fabric, to serve as the back, or inwardly facing bottom layer, of the surgical gown, drape or other garment. Preferably, this layer 14 is also selected of polyester, nylon, cotton, terrycloth, polypropylene, brushed polyester, brushed nylon, brushed cotton, or a blend thereof in woven or knit form. As with the fabric layer 10, the layer 14 can similarly be treated with different finishes to achieve such desirable properties as low lint, high abrasion resistance, high absorbency, and antistatic characteristics, water and other fluid repellency, etc. In one construction of the invention, a polyester tricot of weight substantially 2.0±0.02 oz/yd$^2$ was selected for this third layer 16.

In the preferred embodiment of the invention, the two layers 10 and 12, are laminated together using a non-flammable solvent-based urethane adhesive of any manufacture. Such layers can be laminated by any conventional method for laminating membranes onto fabrics—e.g. powder lamination, hot melt lamination, wet adhesive lamination, etc. In a preferred embodiment of the invention, the lamination can be effected by using a cross-hatch, line-gravure or dot-roller, with the adhesive being used comprising a two component polyurethane system. In such manner, the adhesive was applied to the face fabric 10, with the microporous polyurethane membrane 12 then being laminated by the adhesive to the face fabric. The laminate adhesively secured the two layers 10, 12 together in this manner, and was cured using heat for reactivation, and allowed to stand for 24 hours thereafter to complete the curing process. A high water vapor permeability was produced in this manner, and gave a high level of bond strength to insure that the adhesive lamination thus resulting remained intact after commercial machine laundering and autoclaving. This laminate thus formed a composite material of the trilaminate.

To complete the construction of the trilaminate fabric for use in surgical gowns, surgical drapes or other surgical garments, the second layer 12 was then adhesively laminated to the third layer 14 in much the same way as the layers 10 and 12 were laminated. Thus, an adhesive employing a two component polyurethane system was applied to the membrane 12 and the layer 14 using a cross-hatch, line-gravure, or dot-roller method. After this lamination, the entire trilaminate was cured using heat for reactivation, and allowed to stand for 24 hours to complete the curing process.

In the preferred embodiment of this invention, a completed construction was finalized using adhesive mixtures formed of the composition:

1) polyurethane adhesive of viscosity 5,000 cps±2,000 cps—16.67% by weight; and 2) polyether adhesive of viscosity 15,000 cps±1,000 cps—83.33% by weight.

Such adhesives are generally available and manufactured by Soluol Chemical Co., Inc. of West Warwick, R.I., under the Tradenames Solubond 1101 and Solubond 61-300S, respectively.

To test the efficacy of the 3-layer fabric construction, such fabric was subjected to standard test methods for Moisture Vapor Transmission (ASTM E-96 B and BW), Hydrostatic Resistance (FTMS 191A-5512), Blood Resistance (ASTM ES21) and Virus Resistance (ASTM ES22 [x 174 Challenge Test]). With the test for Moisture Vapor Transmission, a permeability of 1,100 gm/m$^2$/24 hrs was obtained for "upright" testing, and 5,500 gm/m$^2$/24 hrs for "inverted" Moisture Vapor Transmission. With respect to the Hydrostatic Resistance Testing, a resistance of 140 psi was determined—substantially in excess of the 50 psi requirement as the minimum needed for determining a membrane to be both waterproof and breathable. With respect to the Blood Resistance Test, the trilaminate passed the "Challenge Test" for blood, proving that the trilaminate represents an effective barrier to blood-borne bacteria. With respect to the Virus Resistance Test, the trilaminate of the invention was found to be completely protective against virus transmission even when challenged with the smallest known virus X 174.

To test the 3-layer fabric construction of the invention for "shrinkage" and "dimensional stability", the trilaminate was placed in an available washing machine of the type used in commercial operations and run through its flush, suds, rinse, drain and sour cycles—each cycle being followed by a "drying" at 160° before the wash cycle was repeated. It was found that even after 50 cycles, the trilaminate continued to be satisfactory for its intended use as a reusable, durable surgeon gown, surgical drape or surgical garment. Further subjecting the fabric to sterilization in an autoclave for 5 minutes at 275 degrees Fahrenheit similarly showed the trilaminate to continue to be usable for this surgical, or operating room, use.

While there have been described what are considered to be preferred embodiments of the present invention, it will be readily appreciated by those skilled in the art that modifications can be made without departing from the scope of the teachings herein. Thus, whereas the present invention has been specifically described in the context of its use for surgical gowns, surgical drapes and surgical garments, it will be appreciated that the laminate of the invention can likewise be employed for use in protective apparel which also is exposed to adverse climate conditions—e.g. rainwear, skiwear, and the like. Thus, although the invention has been described with emphasis upon its use in meeting OSHA regulations regarding occupational exposure to blood-borne pathogens, it will be understood that the teachings of the invention are suitable for any clothing or apparel where it may be desirable (or necessary) to prevent fluids from penetrating through to the wearer's skin. With this recognition, resort should be had to the claims appended hereto for a true understanding of the scope of the invention.

I claim:

1. A washable, sterilizable article for hospital and/or medical garments which exhibits a very high resistance to the penetration of fluid, blood and virus while exhibiting a high rate of moisture vapor transmission, comprising:

a first layer of one of woven or knit fabric;

a second layer of a microporous polyurethane membrane;

a third layer of one of woven or knit fabric;

a first polyether-polyurethane adhesive joining said first and second layers together;

and a second polyether-polyurethane adhesive joining said second and third layers together; and wherein said second layer comprises a microporous polyurethane membrane composed of a the order of substantially 6 Billion individual pores per square inch.

2. The article of claim 1 wherein said first and second polyether-polyurethane adhesives include adhesive mixtures composed of the formulation by weight of:

a) polyurethane adhesive of viscosity 5,000 cps±2,000 cps—16.67% by weight; and b) polyether adhesive of viscosity 15,000 cps±1,000 cps—83.33% by weight.

3. The article of claim 1 wherein said microporous polyurethane membrane is substantially 0.030–0.055 mm in thickness.

4. The article of claim 1 wherein said first layer is selected from the group consisting of polyester, nylon, cotton, terrycloth, polypropylene, brushed polyester, brushed nylon, brushed cotton, or a blend thereof in woven or knit form.

5. The article of claim 1 wherein said third layer is selected from the group consisting of polyester, nylon, cotton, terrycloth, polypropylene, brushed polyester, brushed nylon, brushed cotton, or a blend thereof in woven or knit form.

6. The article of claim 1 wherein each of said first and third layers is selected from the group consisting of polyester, nylon, cotton, terrycloth, polypropylene, brushed polyester, brushed nylon, brushed cotton, or a blend thereof in woven or knit form.

7. The article of claim 1 wherein said first layer is composed of a plain weave polyester of weight substantially $3.0 \pm 0.02$ oz/yd$^2$.

8. The article of claim 1 wherein said third layer is composed of a polyester knit tricot of weight substantially $2.0 \pm 0.02$ oz/yd$^2$.

* * * * *